US005696000A

United States Patent [19]
Krivan et al.

[11] Patent Number: 5,696,000
[45] Date of Patent: Dec. 9, 1997

[54] ADHESION RECEPTORS FOR PATHOGENIC OR OPPORTUNISTIC MICROORGANISMS

[75] Inventors: Howard C. Krivan; James E. Samuel, both of Derwood, Md.

[73] Assignee: Antex Biologics Inc., Gaithersburg, Md.

[21] Appl. No.: 275,702

[22] Filed: Jul. 18, 1994

Related U.S. Application Data

[60] Continuation of Ser. No. 78,660, Jun. 21, 1993, abandoned, which is a division of Ser. No. 562,002, Aug. 2, 1990, abandoned.

[51] Int. Cl.[6] .................................................. G01N 33/53
[52] U.S. Cl. .................... 435/732; 435/7.33; 435/7.8; 435/7.9; 435/975; 436/501; 436/518
[58] Field of Search ..................... 435/5, 7.32, 882, 435/885, 975, 7.33, 7.8, 7.9, 822, 842, 851, 871, 874, 518; 530/387.1, 389.1

[56] References Cited

U.S. PATENT DOCUMENTS

| | | | |
|---|---|---|---|
| 4,034,074 | 7/1977 | Miles | 424/1 |
| 4,134,792 | 1/1979 | Boguslaski et al. | 195/99 |
| 4,271,140 | 6/1981 | Bunting | 424/1 |
| 4,299,916 | 11/1981 | Litman et al. | 435/6 |
| 4,376,110 | 3/1983 | David et al. | 436/513 |
| 4,464,360 | 8/1984 | Leffler et al. | 514/54 |
| 4,474,892 | 10/1984 | Murad | 436/513 |
| 4,610,868 | 9/1986 | Fountain et al. | 424/1.21 |
| 4,657,849 | 4/1987 | Kallenius et al. | 435/7.3 |
| 4,661,347 | 4/1987 | Tuomanen | 424/137.1 |
| 4,762,713 | 8/1988 | Anderson | 424/92 |
| 4,762,824 | 8/1988 | Kallenius et al. | 514/54 |
| 4,786,592 | 11/1988 | Deal et al. | 424/249.1 |
| 4,795,803 | 1/1989 | Lindberg et al. | 530/324 |
| 4,859,769 | 8/1989 | Karlsson et al. | 514/25 |
| 5,217,715 | 6/1993 | Krivan et al. | 435/252.1 |

FOREIGN PATENT DOCUMENTS

| | | |
|---|---|---|
| 0 126 043 A1 | 11/1984 | European Pat. Off. . |
| 0 352 766 A2 | 1/1990 | European Pat. Off. . |
| PCT/US 91/05179 | 12/1991 | WIPO . |

OTHER PUBLICATIONS

Deal et al., *J. Biol. Chem.* 265:12774–12777 (1990).
Siddiqui et al., *Biochimica et Biophysica Acta.* 330:147–155 (1973).
Karlsson et al., *J. Biol. Chem.* 254:9311–9316 (1979).
Zielenski et al., *Eur. J. Biochem.* 125:323–329 (1982).
Myoga et al., *Cancer Research* 48:1512–1516 (1988).
Krivan et al., *Proc. Natl. Acad. Sci. USA* 85:6157–6161 (1988).
Stromberg et al., *Proc. Natl. Acad. Sci. USA* 85:4902–4906 (1988).
Kaise et al., *Vox Sang.* 49:292–300 (1985).
Tuomanen et al., *J. Exp. Med.* 168:267–277 (1988).
Hultgren et al., *Proc. Natl. Acad. Sci. USA* 86:4357–4361 (1989).
Jacobs et al., *Biochimica et Biophysica Acta.* 832:148–155 (1985).
Enerback et al., *Journal of Clinical Microbiligy* 25/2:407–411 (1987).
Inokuchi et al., *Journal of Cellular Physiology* 141:573–583 (1989).
De Man et al., *Journal of Clinical Microbiology* 25/2:401–406 (1987).
Wold et al., *Infection and Immunity* 56/10:2531–2537 (1988).
Lomberg et al., *Infection and Immunity* 51/3:919–926 (1986).
Lindberg et al., *Nature* 328:84–87 (1987).
Ono et al., *Infection and Immunity* 57/3:907–911 (1989).***
Taki et al., *J. Biochem.* 95:291–294 (1984).
McBroom et al., *Methods in enzymology* 28B:212–219 (1972).
Hakomori, Sen–Itiroh, *Methods in Enzymology* 28B:232–236 (1972).
Stromberg et al., *J. Biol. Chem.* 265:11244–11250 (1990).
Stromberg et al., *FEBS Letters* 232:193–198 (1988).
Bock et al., *J. Biol. Chem.* 260:8545–8551 (1985).
Paruchuri et al., *Pro. Natl. Acad. Sci. USA* 87:333–337 (1990).
Andersson et al., *Monogr. Allergy* 24:44–45 (1988).
Andersson et al., *Microbial. Pathogensis* 4:267–278 (1988).
Ando et al., *J. Biochem.* 79:625–632 (1976).
Gruner et al., *Biochemistry* 24:2833–3842 (1985).
Jimenez–Lucho et al., *Infection and Immunity* 58:2085–2090 (1990).
Krivan et al., *Archives of Biochemistry and Biophysics* 260:493–496 (1988).
Roberts et al., *J. Biol. Chem.* 264:9289–9293 (1989).

(List continued on next page.)

*Primary Examiner*—Donald E. Adams
*Assistant Examiner*—Patricia A. Duffy
*Attorney, Agent, or Firm*—Pennie & Edmonds

[57] ABSTRACT

Disclosed herein are receptors for pathogenic or opportunistic microorganisms, methods of obtaining such reeptors, and methods of using such receptors for diagnostic or pharmaceutical purposes. The receptor comprises a substantially pure compound selected from the group consisting of GalB1-4GlcNAcB1-3GalB1-4GlcB1-1-X(R), GalB1-3GlcNAcB1-3GalB1-4GlcB1-1-X(R), GlcNAcB1-3GalB1-4GlcB1-1-X(R), GalB1-4GlcNAcB1-3GalB1-4Glc, GalB1-3GlcNAcB1-3GalB1-4Glc, GlcNAcB1-3GalB1-4Glc, GalB1-4GlcNAcB1-3Gal, and GalB1-3-GlcNAcB1-3Gal wherein X is sphingosine, hydroxylated sphingosine, or saturated sphingosine and R is H or an N-acyl fatty acid derivative of X such that X(R) is a ceramide. The invention further comprises proteins and polypeptides that bind to the receptors, methods of obtaining such proteins or polypeptides from natural sources or through recombinant DNA techniques, and methods of using the purified proteins and polypeptides for pharmaceutical and diagnostic purposes, preferably in a vaccine for administration to an animal or human host to protect against pathogenic or opportunistic microorganisms.

26 Claims, 4 Drawing Sheets

OTHER PUBLICATIONS

Kyogashima et al., *Archives of Biochemistry and Biophysics* 270:391–397 (1989).

Krivan et al., *J. Biol. Chem.* 264:9283–9288 (1989).

Gubish, Jr., et al., *Infection and Immunity* 37:189–194 (1982).

Pearce et al., *The Journal of Clinical Investigation* 61:931–943 (1978).

Handsfield, "Neisseria Gonorrhoeae, *Infectious Diseases and Their Etiologic Agents*" pp. 1613–1631.

"Neisseria Gonorrhoeae" *Medical Bacteriology* pp. 384–392.

Seifert et al., *Journal of Bacteriology* 172:40–46 (1990).

Andersson et al., *J. Exp. Med.* 158:559–570 (1983).

ADHESION RECEPTORS FOR PATHOGENIC OR OPPORTUNISTIC MICROORGANISMS

This is a continuation of application Ser. No. 08/078,660, filed Jun. 21, 1993, now abandoned which is a divisional of application Ser. No. 07/562,002, filed Aug. 2, 1990 now abandoned.

FIELD OF THE INVENTION

This invention relates to certain receptors for pathogenic and opportunistic microorganisms. The receptors may be used in compositions, kits, apparatus, and methods for detecting or measuring pathogenic or opportunistic microorganisms, removing such microorganisms from a liquid, and treating illnesses or infection or other illness caused by such microorganisms.

The invention further relates to an isolated microbial adhesin protein that binds to the receptors and to methods of obtaining such protein. Such methods include the production of the recombinant protein by genetic engineering means. The protein is expected to be useful in diagnostic and therapeutic composition and particularly in a vaccine for the protection of a human or animal host from infection or other disease caused by pathogenic or opportunistic microorganisms.

REFERENCES

Several publications are referenced herein by Arabic numerals within parenthesis. Full citations for these references may be found at the end of the specification immediately preceding the claims. The disclosures of these publications are hereby incorporated herein by reference in their entirety, unless otherwise noted.

BACKGROUND OF THE INVENTION

The process by which microorganisms bind to host cells is called adherence or adhesion, and it is now generally well accepted that this mechanism is an important step in the initiation of microbial colonization and infection. It has been known for a long time that specific adhesion of bacteria, fungi, mycoplasmas, and viruses to host cells is mediated by cell surface carbohydrate structures (1,2). This is not surprising because all animal and human cells are sugar-coated. That is, they are all covered with a layer of carbohydrate that occurs in the form of glycoproteins and glycolipids which are anchored in the cell membrane and are the glycomolecules that many microorganisms first come into contact with during the infection process. Generally, the structures on the microorganism that mediate binding of infectious agents to host cells are called adhesins, and the host cell carbohydrate structures recognized by microbial adhesins are called the receptors. Therefore, the presence of receptors on host tissue is just as much as a determinant of microbial infectivity as is the microorganisms display of adhesins.

Cell surface carbohydrates have been implicated as receptors for infection based mainly by indirect studies, such as the inhibition of microbial adhesion or hemagglutination by simple sugars and/or by the pretreatment of cells with carbohydrate-splitting enzymes called glycosidases (2,3). Only recently has a more systematic study been conducted using direct binding assays. One such assay involves overlaying glycolipid chromatograms with labeled microorganisms, and, in this way, a number of glycolipids may be shown to bind to a particular bacterium or virus. Because glycolipids contain one oligosaccharide per molecule (unlike glycoproteins which contain several different saccharides per molecule), the specific carbohydrate receptor sequence is much more easily determined (4). Using the overlay technique, it was demonstrated that the *E. coli* that cause urinary tract infections in humans bind to Gal-alpha-1-4Gal-containing glycolipids (5). This result was the impetus for a more thorough investigation of glycolipids as receptors for infectious agents and toxins.

To date, glycolipid receptors have been described for a variety of microorganisms and toxins. For example, species of Propionibacterium bind to lactosylceramide (GalB1-4Glcβ1-1Cer) (6,7), many pulmonary pathogenic microorganisms, including *Pseudomonas aeruginosa, Haemophilus influenzae*, and *Streptococcus pneumoniae*, bind to ganglio-series glycolipids containing GalNacB1-4GalB1-4Glc sequences (8), and *Mycoplasma pneumoniae* binds to sulfated glycolipids containing $Gal(3So_4)\beta1-1Cer$ sequences (9). In addition, it has been reported that *Streptococcus pneumoniae* binds to glycolipids containing the disaccharide GlcNAcβ1-3Gal (10, 11). Recently, *Neisseria gonorrhoeae* has also been reported to bind to ganglio-series glycolipids containing GalNAcβ1-4Galβ1-4Glc sequences (12,13).

The inventors have discovered still another receptor that, surprisingly, appears to be a universal receptor for pathogenic and opportunistic microorganisms. With such a receptor, a purified universal adhesin protein, the gene or genes coding for it, and recombinant proteins produced by such genes are obtained. The protein will be useful in a broad spectrum vaccine against these microorganisms as well as in diagnostic and therapeutic compositions.

SUMMARY OF THE INVENTION

It is an object of the invention to provide receptors for pathogenic or opportunistic microorganisms.

It is another object of the invention to provide compositions useful as receptors for pathogenic or opportunistic microorganisms.

A further object of the invention is to provide diagnostic kits and methods for detecting the presence of pathogenic or opportunistic microorganisms in a sample.

Yet another object of the invention is to provide a method and apparatus for removing pathogenic or opportunistic microorganisms from a liquid.

Still another object of the invention is to provide pharmaceutical methods and compositions for the treatment, prevention, or amelioration of illness or infection in animals caused by pathogenic or opportunistic microorganisms.

A further object of the invention is to provide an isolated microbial adhesin protein useful in diagnostics, therapeutics, and vaccines.

A still further object of the invention is to provide DNA coding for the microbial adhesin protein, Vectors containing the DNA, and microorganisms transformed by such DNA and vectors.

Additional objects and advantages of the invention will be set forth in part in the description that follows, and in part will be obvious from the description, or may be learned by the practice of the invention. The objects and advantages of the invention will be attained by means of the instrumentalistics and combinations particularly pointed out in the appended claims.

To achieve the objects and in accordance with the purpose of the invention, as embodied and broadly described herein, the present invention provides a receptor for a pathogenic or opportunistic microorganism comprising a substantially pure compound selected from the group consisting of Galβ1-4GlcNAcβ1-3Galβ1-4Glcβ1-1-X(R), Galβ1-3GlcNAcβ1-3Galβ1-4Glcβ1-1-X(R), GlcNAcβ1-3Galβ1-4Glcβ1-1-X(R), Galβ1-3GlcNAcβ1-3Galβ1-4Glc, GlcNAcβ1-3Galβ1-4Glc, Galβ1-4GlcNAcβ1-3Gal, and Galβ1-3-GlcNAcβ1-3Gal where X is sphingosine, hydroxylated sphingosine, or saturated sphingosine and R is H or an N-acyl fatty acid derivative of X such that X(R) is a ceramide. Preferably, such receptor is a pure compound from the preceding group attached to a soluble or insoluble substrate. Most preferably, the receptor is attached to a liposome.

In another embodiment, the invention comprises a method for detecting the presence of pathogenic or opportunistic microorganisms in a sample suspecting of containing such microorganisms. The sample is contacted with receptors of the invention for a period of time and under conditions sufficient for the receptors to bind to the microorganisms if they are present in the sample. A determination is then made whether or not the receptors have bound to the microorganisms. Preferably, the receptors are attached to an insoluble substrate and the complexes are detected by a detectably labeled antibody to an antigen on the surface of the microorganism.

The invention further comprises a diagnostic kit for the detection of these microorganisms in a sample. The kit contains the receptors of the invention attached to an insoluble support and means for detecting or measuring the formation of complexes of the receptors and the microorganisms or the receptors and the adhesin proteins from the microorganisms. The kit is particularly useful for detecting pathogenic or opportunistic microorganisms in a sample that is a body fluid from a human or other animal. Preferably, the means for detecting or measuring the complexes is an immunoassay.

In another aspect, the invention is a method and apparatus for removing these microorganisms from a liquid.. The liquid is contacted with the receptors of the invention for a period of time and under conditions sufficient to bind the receptors to the microorganisms. The liquid is then removed from contact with the receptors, thereby removing the microorganisms from the liquid. The related apparatus comprises a container for holding the liquid, means for introducing the liquid into a container, and means for removing it from the container. The container contains the receptors of the invention, preferably bound to a solid support within the container.

The invention further comprises methods and pharmaceutical compositions for the treatment, prevention, or amelioration of infection or other diseases in humans and other mammals caused by pathogenic or opportunistic microorganisms. An effective amount of the receptors of the invention for such treatment, prevention, or amelioration is administered to the mammalian host, preferably in combination with a pharmaceutically acceptable carrier. Preferably, the carrier is a liposome. In an alternative preferred embodiment, the carrier is a macromolecule to which the receptor has been coupled. In a particularly preferred embodiment, the receptor is dissolved or suspended in a liquid that is physiologically compatible with mammalian cells and such composition is used to inhibit the adherence of pathogenic or opportunistic microorganisms to such cells or to remove such microorganisms from such cells.

In still another embodiment, the invention provides a substantially pure microbial adhesin protein, obtained from the surface of a pathogenic or opportunistic microorganism, that binds to the receptors of the invention. The protein is obtained by solubilizing the membranes of pathogenic or opportunistic microorganisms. The solubilized material contains the adhesin protein. This material is separated from the insoluble material and contacted with the receptors of the invention for a period of time sufficient for the protein molecules to bind to the receptors. The receptors are attached to an insoluble solid support. The protein molecules are then removed from the receptors and recovered. Preferably, the receptors are washed after being contacted with the solubilized material to remove unbound material completely.

The invention also includes modified proteins and polypeptides derived from the adhesion protein, provided such derived proteins and polypeptides bind to the receptors of the invention. Preferably, such derivatives are one or more of the epitopes of the adhesin protein. Preferably, they are also immunogenic for human or animal hosts and immunologically cross reactive with the bacterial adhesin protein. In a particular preferred embodiment, the polypeptide has been altered to enhance its immunogenicity.

The polypeptides are useful in a vaccine for preventing, ameliorating, or treating infection or other disease in a human or animal host. In a preferred embodiment, the vaccine comprises an immunologically effective amount of a protein or polypeptide of the invention in a pharmaceutically acceptable carrier. In an alternative preferred embodiment, the vaccine comprises an avirulent microorganism which has been genetically engineered to express a protein or polypeptide of the invention.

The proteins and polypeptides of the invention are preferably recombinant proteins and polypeptides that have been produced through genetic engineering techniques. They are produced by an appropriate host cell that has been transformed by DNA that codes for such proteins or polypeptides.

An isolated or substantially pure DNA sequence that codes for the microbial adhesin protein of the invention is obtained as follows. Receptors of the invention are used to screen a genomic library containing the DNA of a pathogenic or opportunistic microorganism. The library is made of clones of vectors into which different sequences of the DNA have been operably and recoverably inserted, with each of the vectors containing only one sequence of the DNA. The clones are contacted with the receptors of the invention to identify a clone that binds to the receptors. The clone is then isolated. Preferably, the exogenous DNA sequences are recovered from the clone.

The invention further comprises isolated or substantially purified DNA derived from this DNA, for example, by single or multiple mutations. Preferably, such DNA hybridizes with the DNA obtained from the genomic library under conditions of moderate stringency.

The accompanying drawings, which are incorporated in and constitute a part of this specification, illustrate one embodiment of the invention and, together with the description, serve to explain the principles of the invention.

BRIEF DESCRIPTION OF THE DRAWINGS

FIGS. 1A and 1B show the binding of $^{125}$I-labeled *N. gonorrhoeae* strain MS11$_{mk}$ (P-, PII-) to paragloboside and lacto-N-triaosylceramide separated by thin-layer chromatography. Glycolipids were chromatographed on aluminum-backed silica gel HPTLC plates developed in chloroform/methanol/0.25% KCl in water, 5:4:1. The plates were coated with 0.1% polisobutylmethacrylate, soaked in TBS-BSA, and incubated for 2 h at 25° C. with $^{125}$I-labeled gonococci suspended in HBSS-BSA (panel 1B), or sprayed with orcinol reagent to identify glycolipids (Panel 1A). Lanes 1, 1 ug each galactosylceramide (CMH), lactosylceramide doublet (CDH), trihexosylceramide (CTH), globoside (GL4), Forssman glycolipid (FORS), and gangliosides GM3, GM2, GM1, GD3, GD1a, GD1b, and GT1b; lanes 2, 1 ug sialylparagloboside; lanes 3, 1 ug paragloboside derived from sialylparagloboside by treatment with neuraminidase; lanes 4, lacto-N-triaosylceramide derived from paragloboside by treatment with beta-galactosidase; lanes 5, 1 ug lactosylceramide derived from lacto-N-triaosyl-ceramide by treatment with N-Acetyl-B-hexosaminidase. For structures see Table I.

FIG. 2 shows the binding of *N. gonorrhoeae* strain MS11$_{mk}$ (P-, PII-) to immobilized glycolipids. Lipids in 25 ul of methanol containing 0.1 ug each of the auxiliary lipids cholesterol and phosphatidylcholine were evaporated in flat-bottom wells of polyvinylchlorine microtiter plates. The wells were blocked with 1% albumin overnight at 4° C., washed twice with HBSS-BSA and incubated at 25° C. with 25 ul of $^{125}$I-labeled *N. gonorrhoeae* (approximately $10^5$ cpm). After 2 h, the wells were washed 5 times with saline, cut from the plate, and bound radioactivity quantified in a scintillation counter. In control experiments gonococci were incubated with auxiliary lipids only to correct for nonspecific binding (typically <1% of the total radioactivity added). *N. gonorrhoeae* binding was determined in HBSS-BSA for asialo-GM2(■), paragloboside (▲) and lactosylceramide, GM1 or sialylparagloboside (□).

FIGS. 4A and 4B show the binding of *Pseudomonas aeruginosa* CT4 to glycolipids separated by thin layer chromatography. Glycolipids were chromatographed on aluminum-backed silica gel HPTLC plates developed in chloroform/methanol/0.25% KCl in water, 5:4:1. The plates were coated with polyisobutylmethacrylate, soaked in Tris-BSA, and incubated for 2 h at 25° C. with $^{125}$I-labeled *P. aeruginosa* suspended in Tris-BSA containing 1% BSA. FIG. 4A shows standard glycolipids detected with orcinol reagent. FIG. 4B shows glycolipid receptors detected by overlaying with radiolabeled microorganisms followed by autoradiography (18 h). Lanes 1, galactosylceramide (CMH), lactosylceramide (CDH), sulfatide (SFT), globtriaosylceramide (CTH), globoside (GL4), and gangliosides GM3, GM2, GM1, GD1a, GD1b, and GT1b (1 ug of each glycolipid); lanes 2, gangliotriaosylceramide (asialo-GM2, 1 ug) and gangliotetraosylceramide (asialo-GM1, 1 ug); and lanes 3, lacto-N-tetraosylceramide doublet (paragloboside, 2 ug).

DETAILED DESCRIPTION OF THE INVENTION

Reference will now be made in detail to the presently preferred embodiments of the invention, which, together with the following examples, serve to explain principles of the invention.

The invention relates to a universal adhesion receptor for pathogenic or opportunistic microorganisms, microbial adhesin proteins and polypeptides that bind to the receptor, DNA coding for the proteins, and methods of using these materials. As used herein, the terms "adhesin receptor" or "receptor" mean a compound that has a specific affinity for and selectively binds to one or more types of microorganism.

The receptor comprises certain lacto-series glycolipids and derivatives thereof that act as adhesion receptors to a broad and diverse spectrum of microorganisms. One of the glycolipids is lactotriaosylcer (lactotriaosylceramide, N-acetylglucosamine-beta 1-3-galactose-beta 1-4-glucose-beta 1-1-ceramide), which is represented by the following formula:

GlcNAcB1-3GalB1-4GlcB1-1Cer

Another is paragloboside (lactoneotetraosylceramide, galactose-beta 1-4-N-acetylglucosamine-beta-1-3-galactose-beta 1-4-glucose-beta-1-1-ceramide), which is represented by the following formula:

GalB1-4GlcNAcB1-3GalB1-4GlcB1-1Cer

A third is an isomer of paragloboside, which is represented by the following formula:

GalB1-3-GlcNAcB1-3GalB1-4GlcB1-Cer (Trivial names and structures are represented according to the recommendations in Reference 38 and the references cited therein. As used in the formulas in this application, B equals beta.) In addition, the receptors of the invention include the above-referenced compounds from which the fatty acid moiety of the ceramide moiety has been removed. Finally, the receptors of the invention include the carbohydrate moieties of the above-referenced structures and certain residues-thereof. These are represented by the following formulas:

GalB1-4GlcNAcB1-3GalB1-4Glc

GalB1-3GlcNAcB1-3GalB1-4Glc

GlcNAcB1-3GalB1-4Glc

GalB1-4GlcNAcB1-3Gal

GalB1-3GlcNAcB1-3Gal

The preferred receptor structure is GlcNAcB1-3GalB1-4GlcB1-1Cer.

Therefore, the receptors of the invention comprise a substantially pure compound selected from the group consisting of GalB1-4GlcNAcB1-3GalB1-4GlcB1-1-X(R), GalB1-3GlcNAcB1-3GalB1-4GlcB1-1-X(R), GlcNAcB1-3GalB1-4GlcB1-1-X(R), GalB1-4GlcNAcB1-3GalB1-4Glc, GalB1-3GlcNAcB1-3GalB1-4Glc, GlcNAcB1-3GalB1-4Glc, GalB1-4GlcNAcB1-3Gal, and GalB1-3-GlcNAcB1-3Gal wherein X is sphingosine, hydroxylated sphingosine, or saturated sphingosine and R is H or an N-acyl fatty acid derivative of X such that X(R) is a ceramide.

The receptors of the invention are at least substantially pure and preferably pure. As used herein, the term "substantially pure" and similar terms means that the compound is at least 80% pure by weight. That is, the compound does not contain more than 20% by weight of chemicals other than the compound. As used herein, the term "pure" and related terms means that the receptor compound provides only one band after being analyzed by thin layer chromatography and chemically stained according to the methods described in Reference 9, incorporated herein by reference. If necessary, the compound can be further purified by known techniques. Thus, the receptor compound is at least 90% pure by weight, preferably at least 95% pure by weight, and most preferably at least 98% pure by weight.

As mentioned previously, the receptors of the invention act as adhesion receptors for a broad array of pathogenic or opportunistic microorganisms. As used herein, the term "microorganisms" include bacteria, viruses, mycoplasma, fungi, rickettsiae, and protozoa. Preferably, the microorganisms are bacteria. As used herein, the term "pathogenic microorganisms" means any microorganisms that cause disease (including infection) or morbid symptoms in humans or other animal hosts. As used herein, the term "opportunistic microorganisms" means any microorganisms that do not ordinarily cause disease or infection but which become pathogenic under certain circumstances in which the host organism is stressed, such as having an impaired immune response. Preferably, the receptors of the invention bind to bacteria of the following genera: Strepotococcus, Staphylococcus, Clostridium, Borrelia, Haemophilus, Pseudomonas, Neisseria, Coxiella, and Shigella. Most preferably, the bacteria are the following: *Streptococcus pneumoniae, Streptococcus agalactiae* (Gp. B), *Staphylococcus aureus, Clostridium perfringens, Clostridium difficile, Borrelia burgdorferi* (Lyme agent), *Haemophilus influenzae, Haemophilus parainfluenzae, Pseudomonas aeruginosa, Pseudomonas cepacia, Pseudomonas maltophilia, Neisseria gonorrhoeae, Neisseria meningitidis, Shigella dysenteriae, Shigella flexneri,* and *Coxiella burnetti.* In an alternative preferred embodiment, the microorganisms are rotaviruses.

The inventors have also surprisingly discovered that the disaccharide, GlcNAcB1-3Gal, which has been reported as a receptor for *S. pneumoniae* but not for any of the other microorganisms mentioned above, also acts as a receptor for the other above-referenced microorganisms. Thus, the invention also includes compositions containing this receptor and methods of using it with respect to microorganisms other than *S. pneumoniae.*

The receptors of the invention are prepared by known techniques in conjunction with the teachings disclosed herein. Paragloboside is prepared by desialylation of erythrocyte sialylparagloboside with 1M formic acid for 60 minutes at 100° C. as disclosed in Reference 9. Lactotriaosylcer is prepared by digestion of paragloboside with beta-glactosidase as described for the preparation of asialo-GM2 from asialo-GM1 in Reference 14. The lyso derivatives of these compounds are prepared by techniques disclosed in Basta, M., Karmali, M., and Lingwood, C. (1989) J. Chm. Microbiol. 27: 1617–1622, incorporated herein by reference. The carbohydrate moiety derivatives of these glycolipids are prepared by removing the ceramide moiety according to the techniques of Miljkovic, M. and Schengrund (1986) Carbohydr. Res. 155: 175–181; Ito, M. and Yamagata, T. (1986) J. Biol. Chem. 261: 14278–14282; and Kanfer, J. N. and Hakomori, S-i (1983) Handbook of Lipid Research, Sphingolipid Biochem., Plenum Press, New York, incorporated herein by reference, or synthesized directly according to the techniques of European patent application 84850084.9 of Svenska Sockerfabriks Ab, published Nov. 21, 1984 (Publication No. 0,126,043), incorporated herein by reference. The receptor GlcNAcB1-3GalB1-4Glc is synthesized according to the latter techniques.

The receptors of the invention are useful for detecting the presence of pathogenic or opportunistic microorganisms in a sample suspected of containing such microorganisms. In addition, since adhesins may be secreted by some microorganisms, the presence of the adhesins may be detected with the receptor. The receptors of the invention are contacted with the sample for a period of time and under conditions sufficient for receptors to bind to the microorganisms and/or the adhesins, if either or both are present. Such time and conditions can be readily determined by persons skilled in the art with respect to any particular type of microorganisms, given the teachings described herein. One then determines if the receptors have bound to the microorganisms and/or adhesins, forming microorganism-receptor and/or adhesin-receptor complexes. The binding of the microorganisms and/or the adhesins to the receptors is determined by techniques known to those skilled in the art in conjunction with the teachings disclosed herein.

Preferably, the receptors are bound to a solid matrix or other insoluble substrate. The receptors should be bound to the substrate in an amount and manner that allows sufficient binding of the microorganisms to be detected. Preferably, the receptors are bound as a molecular monolayer that substantially covers the surface of the substrate. The actual concentration of the receptor to a given substrate will depend upon the particular microorganism to be detected, the particular receptor being used, the particular substrate, and the binding efficiency of the receptor to the microorganism.

The receptor may be bound to the substrate in any suitable manner. Covalent, noncovalent, or ionic binding may be used. For example, the lipid portion may be hydrophobically bonded to certain plastic substrates. Covalent bonding can be accomplished by attaching the receptor to reactive groups on the substrate directly or through a linker arm as disclosed in U.S. Pat. No. 4,657,849 to Kallenius et al., incorporated herein by reference. Alternatively, the lyso derivatives of the receptors can be attached to the solid support in accordance with the method disclosed in published European Patent Application No. 89113785.3 (publication no. 0 352 766), filed Jul. 26, 1989 and published Jan. 31, 1990, incorporated herein by reference.

Preferably, the receptor is first coupled to a soluble substrate, such as a protein. Bovine serum albumin is preferred. Then this combination is attached to the insoluble support.

The insoluble substrate may be any solid, insoluble material to which the receptors can be bound and which may be conveniently used in the assay of the invention. Such substrates include permeable and semipermeable membranes, glass beads, plastic beads, latex beads, plastic microtiter wells, agarose, dextran, sepharose and diatomaceous earth. Alternatively, the receptors may be bound to any porous or liquid permeable material, such as a screen or net. A binder may be used as long as it does not interfere with the ability of the receptor to bind microorganisms.

In a particularly preferred embodiment, the receptors are incorporated into liposomes. The liposomes are preferably prepared according to the techniques of Gruner, et al., Biochemistry, 24:2833–2842 (1985), incorporated herein by reference. The receptors are incorporated into the liposomes using standard techniques. They are essentially incorporated spontaneously into the lipid bylayer of the liposome after being contacted with the liposome. The fatty acid part goes into the lipid membrane, and the carbohydrate moiety sticks out of the membrane, interior or exterior to the liposome.

After the sample has been contacted with the substrate containing the receptors for a sufficient period of time to allow the microorganisms to bind to the receptors, such binding is detected through the application of the appropriate detecting means. Basically, the substrate containing the receptors and suspected of containing microorganisms bound to the receptors is contacted with a material that binds specifically to the microorganisms sought to be detected. Such materials include, for example, antibodies against the specific microorganisms, particularly against surface proteins, or a receptor that binds specifically to the microorganisms sought to be detected. Generally, the substrate is washed to remove all or substantially all unbound materials. The detecting assay may be an immunoassay, agglutination assay, thin layer chromatography assay, or cytotoxicity assay. Immunoassays include radioimmunoassays, enzyme-linked immunosorbent assays (ELISA), Western blot, immunofluorescent assays, chemiluminescent assays, and bioluminescent assays. The degree or amount of binding can also be determined through the application of known techniques, providing a measurement of the amount or concentration of microorganisms in the sample.

The antibody or carbohydrate receptor may be labelled with a substance that is easily detected. Such detectable moieties include an enzyme or radioactive, fluorescent, or chemiluminescent entity. A first antibody to a surface antigen of the microorganisms sought to be detected can be used in conjunction with a labelled second antibody to the first antibody. The first antibody is brought into contact with the substrate, binding to any microorganisms bound to receptors on the substrate. The substrate is preferably washed and contacted with the second antibody, which is then detected, thereby indicating the presence of the microorganisms on the substrate.

The various detectable moieties that can be used to label the antibodies or receptors used in such assays, the techniques for doing so, and the various specific assays in conditions for using them are well-known to those skilled in the art. For example, see U.S. Pat. No. 4,486,530 to David et al., issued Dec. 4, 1984, U.S. Pat. No. 4,708,818 to Montagnier et al., issued Nov. 24, 1987, and U.S. Pat. No. 4,753,873 to Beltz et al., issued Jun. 28, 1988, all of which are incorporated herein by reference. A particularly preferred assay incorporating the receptors of the invention is based upon the one disclosed in Basta, et al., *J. Clin. Microbiology*, 27:1617–1622 (1989), incorporated herein by reference.

Various types of samples can be tested for the presence of pathogenic or opportunistic microorganisms in accordance with the invention. The sample may be a biological sample, comprising or derived from a bodily fluid or tissue extract from a human or other animal patient. The sample will normally be diluted with an appropriate solution, such as physiological saline. Alternatively, a cotton swab or other material can be used to collect the microorganisms. The swab is then placed in a sterile solution in order to release the microorganisms into the solution. The solution is then tested in accordance with the invention.

The invention may also be used to test for the presence of microorganisms in environments that should Me sterile, such as hospital operating rooms, drug and medical device manufacturing facilities, and food manufacturing facilities. Microorganisms can be collected by various means known to those skilled in the art, and a liquid sample containing such microorganisms can be prepared.

The invention also comprises kits for detecting the presence of pathogenic or opportunistic microorganisms, which would have utility in scientific research, clinical diagnosis, and food safety procedures. The kit comprises: (1) a container holding a solid support or other insoluble substrate to which the receptors of the invention are attached; and (2) a means for detecting or measuring the formation of complexes of the microorganisms or adhesins and receptors. Alternatively, the receptors may be attached to the walls of the container that are exposed to the sample. Preferably, the insoluble substrate is the well of a microtiter plate. The detecting or measuring means is preferably a reagent containing a detectable moiety and capable of binding to the microorganisms. Such reagent may be the receptor of the invention conjugated with a detectable moiety. Alternatively, the reagent may be an antibody to a surface antigen of the microorganisms conjugated to a detectable moiety, such as an enzyme. In another alternative embodiment, the detecting or measuring means is a first antibody to a surface antigen of the bacterium and a second antibody to the first antibody wherein the second antibody is conjugated to a detectable moiety. An example of such a second antibody is goat anti-IgG labelled with peroxidase.

The invention also comprises methods and apparatus for removing pathogenic or opportunistic microorganisms from a liquid. The liquid is contacted with the instant receptors for a period of time and under conditions sufficient to bind the microorganisms to the receptors. Then the liquid is removed from contact with the receptors or the receptors are removed from contact with the liquid, thus providing a liquid which is free of the microorganisms or in which their number has been substantially reduced, depending upon the degree of removal sought. Preferably, the receptors are attached to a solid support as previously discussed herein and the liquid flows across the receptors.

The related apparatus comprises a container for the liquid with an inlet for introducing the liquid and an outlet for removing it. In addition, the container contains the receptors bound to a solid support or, alternatively, the receptors can be bound to the surface of the container exposed to the liquid. Most preferably, the container is a chromatographic column containing a solid phase matrix to which the receptors of the invention are attached. For example, they may be covalently coupled to epoxy-activated Sepharose (Sepharose-4B, Pharmacia) or a similar agarose-based matrix. The liquid is introduced to the top of the affinity column and the microorganisms are removed as the liquid passes down the column to be collected at the bottom.

In an alternative embodiment, the solid support for the receptors is a membrane, preferably a semipermeable membrane, or a liposome. As the liquid passes through the membrane or liposome, microorganisms are removed.

The receptors may also be used for treating, preventing, or ameliorating illness or infection in a host caused by pathogenic or opportunistic microorganisms. Generally, the receptors are administered in a pharmaceutically compatible carrier. Accordingly, the invention encompasses a pharmaceutical composition for the treatment, prevention, or amelioration of illness or infection in animals, particularly mammals, and most particularly humans, comprising an effective amount of the receptors of the invention for such treatment, prevention, or amelioration in a pharmaceutically acceptable carrier. The receptors may be in admixture with the carrier or coupled to it. For example, receptors may be coupled to a macromolecular carrier. They may also be within liposomes.

The compositions are prepared by techniques known in the art, given the teachings contained herein. The receptors are mixed with additives customary for pharmaceutical purposes, such as vehicles, stabilizers, solubilizers, or inert diluents, and converted by customary methods to a suitable administration form, such as tablets, capsules, solutions, suspensions, or emulsions. If the receptor is coupled to a macromolecular carrier, it is preferred that the carrier be a natural or synthetic polymer. Preferably, such polymer is a polypeptide, such as bovine serum albumin, or a polysaccharide. In a particularly preferred embodiment, the receptors are incorporated into liposomes as previously discussed herein.

The pharmaceutical preparations of the invention are administered locally, as by injection or topical application, intravenously, orally, intradermally, subcutaneously, intraocularly, subconjunctively, intramuscularly, and intrathecally. The mode of administration will necessarily depend upon the disease and microorganisms involved.

An effective amount of the composition is administered to the host or patient. The host or patient is an animal, preferably a mammal, and most preferably a human. The actual amount of the receptor to be administered will depend upon the particular disorder being treated. Such a determination is routinely made by those of ordinary skill in the art of determining therapeutic dosages and is within the scope of tasks routinely performed by them without undue experimentation.

A preferred use of the receptors of the invention is for inhibiting the adherence of pathogenic or opportunistic microorganisms to animal, preferably mammalian, cells or removing such microorganisms from such cells. The cells may be in tissue culture or in the host. A sufficient amount of the receptors of the invention to inhibit the adherence of such microorganisms or to remove such microorganisms are administered to such cells. Preferably, the receptors are dissolved or suspended in a liquid which is physiologically compatible with the cells.

In a particularly preferred embodiment, the receptors are dissolved in saline solution, which is then used to irrigate the wounded tissue of a mammalian host. For example, the tissue may be burned human skin tissue. Irrigation with the liquid helps remove microorganisms that could cause or are causing the wound to be infected.

In an alternative and preferred embodiment of the invention, the soluble substrate to which the receptors are coupled is a pharmaceutical compound directed against a type of pathogenic or opportunistic microorganisms. For example, the compound may be an antibiotic which is needed to treat disease caused by pathogenic bacteria, but which has serious side effects. By coupling the antibiotic to a receptor of the invention, the antibiotic will be targeted to the bacteria in question. This will allow the administration of a much lower, but still therapeutic dose to the host, lowering or eliminating the side affects attributable to the antibiotic. The compound may also be an immunogen that stimulates the production of antibodies against a particular microorganism in the host.

The invention further comprises an isolated microbial adhesin protein, obtained from the surface of a pathogenic or opportunistic bacterium, that binds to the receptors of the invention. The protein is obtained from natural sources, i.e., pathogenic or opportunistic microorganisms that bind to the receptors of the invention, by the application of standard protein purification techniques in view of the teachings contained herein. Alternatively, the protein is obtained as a recombinant protein through the application of standard genetic engineering techniques in view of the teachings contained herein.

The preferred method for producing the isolated protein from natural sources is as follows. Membranes of pathogenic or opportunistic microorganisms are obtained by standard techniques and solubilized, using a solubilizing compound, such as a detergent. The adhesin protein is in the solubilized material. The remaining insoluble material from the membrane is separated, preferably by centrifuging. The supernatant is passed through an affinity chromatography column containing the receptors of the invention, thereby causing the protein to bind to the insoluble matrix of the column. The column is preferably washed one or more times within appropriate buffer solution. The adhesin protein is then eluted using the appropriate agent. This may be free receptor in solution or a chaotropic agent, such as KSCN, NaCl, or quanidine hydrochloride. The eluted protein is then tested against the receptors of the invention to confirm that it does bind to them. The purity of the isolated protein may be analyzed by SDS-PAGE.

If desirable, the protein can be further purified by the application of standard protein purification techniques, modified and applied in accordance with the discoveries and teachings described herein. Such techniques include electrophoresis, centrifugation, gel filtration, precipitation, dialysis, chromatography (including ion exchange chromatography, affinity chromatography, immunoadsorbent affinity chromatography, reverse-phase high performance liquid chromatography, and gel permeation high performance liquid chromatography), isoelectric focusing, and variations and combinations thereof. The preferred techniques include those identified and described in U.S. Pat. No. 4,446,122 issued May 1, 1984 to Chu, et al., which is incorporated herein by reference. Preferably, the protein is further purified by receptor affinity chromatography.

One or more of these techniques are employed sequentially in a procedure designed to separate molecules according to their physical or chemical characteristics. These characteristics include the hydrophobicity, charge, binding capability, and molecular weight of the protein. The various fractions of materials obtained after each technique are tested for their ability to react with the receptors of the invention. Those fractions showing such activity are then subjected to the next technique in the sequential procedure, and the new fractions are tested again. The process is repeated until only one fraction reactive with the receptors remains and that fraction produces only a single band when subjected to polyacrylamide gel electrophoresis.

Thus, the protein of the invention is a substantially pure protein that binds to the receptors of the invention. As used herein, "substantially pure" and related terms mean that the protein has been isolated from other proteins naturally associated with the protein of the invention. The substantially purified protein is at least 80% pure by weight and preferably at least 90% pure by weight. That is, the composition comprising the substantially purified protein contains no more than 20% and preferably no more than 10% by weight of proteins that are not the protein of the invention. Since the protein may be purified further by the application of standard techniques, the invention encompasses the purified protein. As used herein, the term "purified" and variants thereof means that the proteins are at least 95% pure by weight, preferably at least 98% pure by weight, and most preferably at least 99% pure by weight.

The protein of the invention may be modified by known protein modification techniques. These include the techniques disclosed in U.S. Pat. No. 4,302,386, issued Nov. 24, 1981 to Stevens, incorporated herein by reference. Such modifications may enhance the immunogenicity or antimicrobial activity of the protein or it may have no effect on such activity.

For example, a few amino acid residues may be changed or removed. Alternatively, the protein of the invention may contain one or more amino acid sequences that are not necessary to its immunogenicity or antimicrobial activity. It may be the case, for example, that only the amino acid sequences of a particular epitope of the antigen will be necessary for immunogenic activity. Unwanted sequences can be removed by techniques well-known in the art. For example, unwanted amino acid sequences can be removed via limited proteolytic digestion using enzymes such as trypsin or papain or related proteolytic enzymes.

This approach is expected to be particularly useful for the adhesin protein of the invention. Since the receptors of the invention bind to a broad array of microorganisms, the protein adhesins of those microorganisms may have slight variations in their amino acid sequence. However, they all bind to the concensus sequence GlcNAcB1-3GalB1-4GlcB1-1Cer, whether that sequence is a terminal sequence as in lactotraosylcer or an internal sequence as in parglobo-side. Therefore, such proteins will have a conserved region which is a universal epitope. This universal epitope is the particularly preferred polypeptide of the invention.

Alternatively, polypeptides corresponding to various immunogenic epitopes of the protein may be chemically synthesized by methods well-known in the art. These include the methods disclosed in U.S. Pat. No. 4,290,994, issued Sep. 22, 1981 to Goldberg, incorporated herein by reference.

Thus, the protein of the invention includes a class of modified polypeptides, including synthetically derived peptides or fragments of the protein, having common elements of origin, structure, and mechanism of action, such as immunogenic or antimicrobial effect or being able to bind to the receptor of the invention, that are within the scope of the present invention because they can be prepared by persons skilled in the art, once given the teachings of the present invention. Moreover, since persons skilled in the art can make modifications to or derivatives of epitopes on the protein of the invention, once such epitopes are identified, such modifications or derivatives are within the scope of the invention, provided that they are immunogenic and have an antimicrobial effect in humans or other animals, particularly including mammals and primates.

Thus, the polypeptide may be an immunogenic fragment of the protein of the invention or a modified polypeptide substantially homologous to this polypeptide. As used herein, the term "substantially homologous" means immunologically cross-reactive. Such a polypeptide may also be identified by the fact that it will bind to antibodies to the adhesin protein of the invention, which antibodies can be prepared by standard techniques.

The adhesin protein of the invention or an immunogenic fragment or polypeptide derived therefrom is expected to have utility as an immunogen in an antimicrobial vaccine for animals, including mammals, primates, and humans. Such a vaccine can be prepared by techniques known to those skilled in the art and would comprise, for example, the antigen, a pharmaceutically acceptable carrier, an appropriate adjuvant, and other materials traditionally found in vaccines. An immunologically effective amount of the antigen is determined by means known in the art.

Figure 3A:
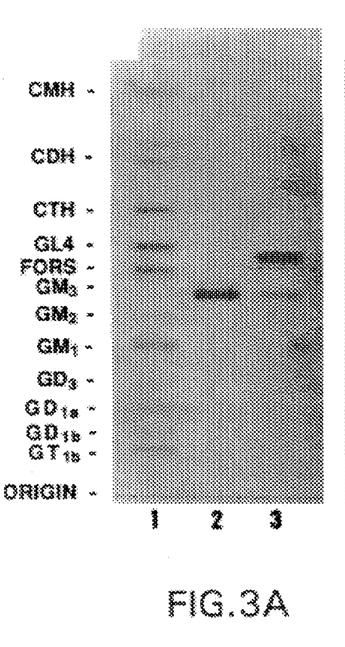
FIGS. 3A and 3B show the binding of anti-LOS monoclonal antibody 4BE12 to authentic paragloboside. Panel 3A, glycolipids detected by orcinol staining. Panel 3B, autoradiogram of chromatogram overlay with monoclonal antibody B54 and radiolabeled anti-mouse IgM antibody. Lanes 1, 1 ug each of galactosylceramide (CMH), lactosylceramide (CDH), trihexoslyceramide (CTH), globoside (GL4), Forssman glycolipid (FORS), and gangliosides GM3, GM2, GM1, GD3, GD1a, GD1b, and GT1b; lanes 2, 1 ug asialo-GM1; lanes 3, 1 ug of paragloboside; lanes 4,5,6,7,8, and 9 are 0.5, 0.25, 0.125, 0.062, 0.031, and 0.016 ug of paragloboside, respectively.
Figure 3B:
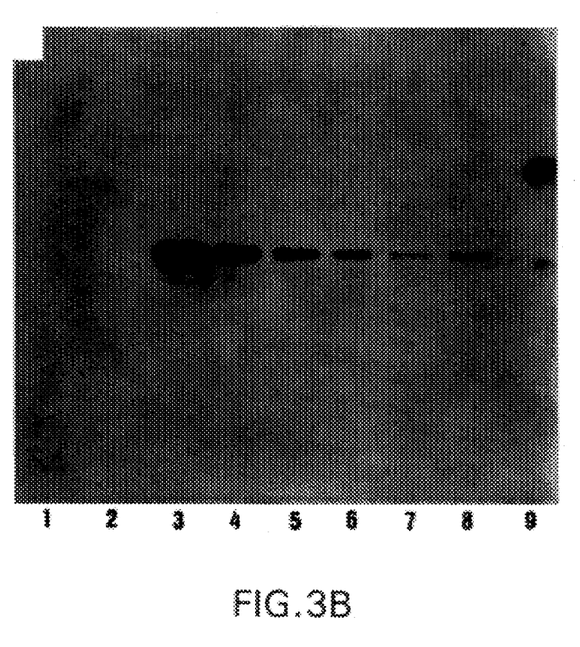

The proteins and polypeptides of the invention may also be used to detect a microorganism that expresses the receptors of the invention. For example, as shown in FIG. 3, *N. gonorrhoeae* was found to contain the receptor GalB1-4GlcNAcB1-3GalB1-4Glc as part of its lipopolysaccharide. Thus, the protein or polypeptide can be attached to a solid support, such as beads or a microtiter well, by standard techniques and employed in methods and kits for the detection of such microorganisms as described previously herein. Similarly, the protein or polypeptide can be attached to a pharmaceutical agent as described previously herein to target such agent to such pathogenic or opportunistic microorganism.

Given the receptors of the invention and the teachings disclosed herein, persons skilled in the art can obtain the DNA that codes for the microbial adhesin polypeptide of the invention in isolated or substantially purified form through the application of standard genetic engineering techniques. Such techniques include those described in Maniatis et al., *Molecular Cloning: A Laboratory Manual* (New York: Cold Spring Harbor Laboratory 1982), incorporated herein by reference.

The DNA of the invention is an isolated or substantially purified DNA sequence (i.e., polydeoxyribonucleotide) encoding a polypeptide that binds to the receptors of the invention. As used herein, the term "isolated" and variations thereof means that the DNA is in isolation from DNA encoding other polypeptides normally accompanying this polypeptide. Thus, the DNA of the invention includes DNA encoding the polypeptide when that DNA has been cloned into a microbial vector, such as a plasmid, or into a viral vector that may be harbored by a bacteriophage, provided that such clones are isolated from clones that contain DNA encoding other polypeptides normally accompanying this one. As used herein, the term "substantially pure" and variants thereof means that the DNA is substantially free of DNA and RNA that does not encode the protein of the invention. That is, there will be no more than about 1% by weight of other DNA and RNA and preferably no more than about 0.2% by weight of other DNA and RNA in any sample that contains the DNA of the invention.

Preferably, the DNA is obtained by using the instant receptors to screen an appropriate genomic library that contains the DNA of a pathogenic or opportunistic microorganism. Such a library comprises colonies of a single type of microorganism, generally bacteria like *E. coli* K12 (HB101), into which pieces of the foreign DNA have been inserted, generally by being incorporated into a plasmid, cosmid, or phage vector compatible with the microorganism. More specifically, the library comprises clones of vectors into which different sequences of the DNA have been operably and recoverably inserted, each of the vectors containing only one sequence of the DNA. The vectors may be plasmids, cosmids, or phage genomes. If necessary because of the type of library being used, segments of DNA will have been inserted into the vectors in a manner that they will be expressed under appropriate conditions (i.e., in proper orientation and correct reading frame and with appropriate expression sequences, including an RNA polymerase binding sequence and a ribosomal binding sequence.) The microorganisms will be ones that do not express the adhesin protein, such as *E. coli* HB101.

Clones from the library are brought into contact with the receptors of the invention to identify those clones that bind to the receptors. Preferably, the library is brought into contact with the receptor on a thin layer chromatography plate to determine which of the microorganisms bind to the receptor. The clones are isolated and the exogenous DNA sequence is recovered from one of the clones. The sequence is evaluated to determine if it encodes the protein.

In a particularly preferred embodiment, the DNA of the invention is obtained by an application and modification of the teachings of Paruchuri, et al., *Proc. Natl. Acad. Sci. USA*, 87:333–337 (1990), incorporated herein by reference. The authors used a different adhesion receptor for *N. gonorrhoeae* to identify and characterize the adhesion protein and the gene.

As applied to this invention, a genomic library of *N. gonorrhoeae* strain MS11 is constructed in the vector pHSS6 (Seifeft, et al., *Proc. Natl. Acad. Sci. USA*, 83:735–739 (1986), incorporated herein by reference) in *E. coli* HB101 (Seifert, et al., *J. Bacteriol.*, 172:40–46 (1990), incorporated herein by reference. A thin layer chromatography overlay assay is used to identify the clones expressing the adhesion protein. The DNA is then obtained in isolated or substantially purified form.

In an alternate preferred embodiment, colonies containing DNA that encodes the microbial adhesin gene(s) would be detected using DYNA Beads according to Olsvick et al., 29th ICAAC, Houston, Tex. 1989, incorporated herein by reference. The previously described glycolipids would be crosslinked to tosylated dyna beads M280 and these receptor-containing beads would then be used to adsorb to colonies expressing the adhesin protein(s). Colonies not expressing the adhesin would be removed by washing, and this process would be repeated to obtain an appropriate enrichment. Putative adhesin expressing colonies would then be plated and confirmed by metabolically labeling each colony with 35S-methionine and testing the ability of the colony to bind to the receptor as previously described. The DNA from several adherring clones would be compared to identify shared sequences and these shared sequences would be further subcloned and characterized as previously described.

In another alternate preferred embodiment, the gene(s) for the specific glycolipid adhesin would be localized and identified by constructing a non-adherent mutants of a specific pathogen. This would be accomplished by creating mutants using a transposable element such as TnPhoA as described in Manoil et al., Proc. Natl. Acad. Sci. U.S.A., 82:81129–8133 (1985), incorporated herein by reference. Alkaline phosphatase positive mutants would indicate mutations within exported proteins. Since the adhesin for each pathogen is presumed to be located on the outer membrane surface and therefore exported, this set of mutants would contain a much reduced subset of mutants. They would then be screened for a loss in binding activity by procedures previously described.

It will be recognized by persons skilled in the art that the DNA sequence for the adhesin protein may be modified by known techniques in view of the teachings disclosed herein. For example, different codons can be substituted that code for the same amino acid as the original codon. Alternatively, the substitute codons may code for a different amino acid that will not affect the immunogenicity or antimicrobial activity of the protein or which may improve its immunogenicity or antimicrobial activity. For example, oligonucleotide directed, site specific mutagenesis or other techniques to create single or multiple mutations, such as replacements, insertions, deletions, and transpositions, as described in Botstein and Shortle, "Strategies and Applications of In Vitro Mutagenesis," *Science*, 229:193–1210 (1985), which is incorporated herein by reference, can be employed. Since such modified DNA can be obtained by the application of known techniques to the teachings contained herein, such DNA is within the scope of the claimed invention.

Moreover, it will be recognized by those skilled in the art that the DNA sequence (or fragments thereof) of the invention can be used to obtain other DNA sequences that hybridize with it under conditions of moderate to high stringency, using general techniques known in the art. Accordingly, the DNA of the invention includes such DNA.

The DNA of the invention may be used in accordance with known techniques, appropriately modified in view of the teachings contained herein, to construct an expression vector, which is then used to transform a microorganism for the expression and production of the polypeptide of the invention. Such techniques include those disclosed in U.S. Pat. No. 4,440,859 issued Apr. 3, 1984 to Rutter et al., U.S. Pat. No. 4,530,901 issued Jul. 23, 1985 to Weissman, U.S. Pat. No. 4,582,800 issued Apr. 15, 1986 to Crowl, U.S. Pat. No. 4,677,063 issued Jun. 30, 1987 to Mark et al., U.S. Pat. No. 4,678,751 issued Jul. 7, 1987 to Goeddel, U.S. Pat. No. 4,704,362 issued Nov. 3, 1987 to Itakura et al., U.S. Pat. No. 4,710,463 issued Dec. 1, 1987 to Murray, U.S. Pat. No. 4,757,006 issued Jul. 12, 1988 to Toole, Jr., et al., U.S. Pat. No. 4,766,075 issued Aug. 23, 1988 to Goeddel, et al., and U.S. Pat. No. 4,810,648 issued Mar. 7, 1989 to Stalker, all of which are incorporated herein by reference.

The DNA of the invention may be joined to a wide variety of other DNA sequences for introduction into an appropriate host cell. The companion DNA would depend upon the nature of the host cell, the manner of the introduction of the DNA into the host cell, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Generally, not all of the hosts will be transformed by the vector. Therefore, it will be necessary to select for transformed host cells. Once selection technique involves incorporating into the expression vector a DNA sequence, with any necessary control elements, that codes for a selectable trait in the transformed cell, such as antibiotic resistance. Alternatively, the gene for such selectable trait can be on another vector, which is used to co-transform the desired host cell. The preferred expression vector for use in the invention is the Bluescript series from Stratogene, Inc. The preferred host cell is DH5 alpha.

The transformed host cells express the proteins or polypeptides of the invention. Such cells are cultured by known techniques, and the proteins or polypeptides are recovered by known techniques. Depending upon the host and expression system used, the recombinant proteins and polypeptides of the invention may be part of a fusion protein produced by the transformed host cells. Such proteins are recovered by known techniques, and the undesired part may be removed by known techniques. Alternatively, the fusion protein itself may be more immunogenic than the recombinant protein or polypeptide alone and, therefore, may itself be used in a vaccine.

In a particularly preferred embodiment, the vaccine of the invention comprises an avirulent microorganism that has been transformed by the DNA of the invention, whereby the transformed microorganism expresses the protein or polypeptides of the invention in a manner such that the delivery of the avirulent transformed microorganism to an animal or human host results in an immune response. Generally, the foreign antigenic determinants are expressed on the surface of the microorganism. Preferably, the microorganism is in a pharmaceutically acceptable carrier. Particularly preferred microorganisms would be species of Salmonella, which can be prepared for the oral delivery of heterologous antigens according to the methods disclosed in Chatfield, et al., *Vaccine*, 7:495–498 (1989), incorporated herein by reference.

It is to be understood that the application of the teachings of the present invention to a specific problem or environment will be within the capabilities of one having ordinary skill in the art in light of the teachings contained herein. Examples of the products of the present invention and processes for their use appear in the following examples.

EXAMPLE 1

Glycolipid Adhesion Receptors for *N. gonorrhoeae*

This Example shows that lacto-series glycolipids containing the minimum carbohydrate sequence GlcNAcB1-3GalB1-4Glc can support adhesion of *N. gonorrhoeae* and that binding is not dependent on pili, protein II (P II), or the presence of lipooligosaccharide (LOS). Interestingly, lacto-series structures are also found in some LOS derived from the outer membrane of *N. gonorrhoeae* (15), which may explain the well-known phenomenon of autogglutination seen with this organism.

Experimental Procedures

Materials. Gonococcal LOS was isolated from acetone-powdered organisms by the hot-phenol method (16,17). Murine IgG monoclonal antibody 4BE12 against meningococcal LOS serotype 3,7,9(18) was provided by Dr. Wendell Zollinger (Walter Reed Army Institute of Research, Washington, D.C.) Affinity-purified goat anti-mouse IgM (Kirkegaard and Perry, Gaithersburg, Md.) was labeled with $^{125}I$ (ICN Biomedicals, Costa Mesa, Calif.) by the Iodo-Gen method (19) to a specific activity of approximately 25 Ci/ug. Bovine testes B-galactosidase, neuraminidase (Arthrobacter ureafaciens) and bovine serum albumin (BSA, fraction V) were purchased from Boehringer Mannheim (Indianapolis, Ind.) N-Acetyl-B-D-hexosaminidase was from Genzyme (Boston, Mass.). All standard ganglioside and neutral glycolipids were from BioCarb Chemicals (Lung, Sweden). Aluminum-backed silica gel high performance thin-layer chromatography plates were purchased from Merck (West Germany). Alpha-2-3Sialyllacto-neotetraosylceramide (sialyparagloboside) was isolated from type 0 human erythrorooytes (20). Lacto-N-neotetraosylceramide (paragloboside) was prepared by desialylation of erythrocyte sialylparagloboside with 1M formic acid for 60 min at 100° C.. Lacto-N-triaosylceramide was prepared by digestion of paragloboside with B-galactosidase as described for the preparation of asialo-GM2 from asialo-GM1 (14). The concentrations of glycolipids listed in Table I were determined by densitometry (Quick-scan, Helena Laboratories) of orcinol-stained thin-layer chromatograms compared with authentic standards. The purity of all lipids was confirmed by thin-layer chromatography in neutral and acidic solvent systems.

Growth and Labeling of *N. gonorrhoeae*. The gonococcal strains and variants are described in Table II. The microorganisms were grown in supplemented GCB (Difco) broth with shaking at 1500 rpm or on agar plates at 37° C. in 5% $CO_2$/95% air. Cells grown anaerobically on GCB agar were supplemented with nitrate, as described (21). Gonococci grown under iron-limited conditions was done by passing the cells three times on media supplemented with 25 uM Desferal (Ciba-Geigy), as described (22). Microorganisms were scraped from agar plates, or harvested from both by centrifugation, and suspended in 0.01M sodium phosphate, pH 7.4, containing 0.15M sodium phosphate (PBS). Microorganisms were centrifuged at 4° C. and 10,000×g and pellets were washed twice in PBS. The cells were radioiodinated as described (23) using 0.4 mCi of $Na^{125}I$ (ION Biomedicals). The iodination was terminated after 3 min by removing the cells from the reaction tube, followed by centrifugation and two washes in PBS. The labels gonococci were resuspended to $2.5 \times 10^6$ or $4 \times 10^6$ cpm/ml in Hanks Balanced Salt Solution, pH 7.4, containing 1% bovine serum albumin (HBSS-BSA).

Assay of *N. gonorrhoeae* Binding to Glycolipids. Gonococci bound to glycolipids separated by high performance thin-layer chromatography were detected as described (23). The binding of gonococci to purified glycolipids immobilized in microtiter plates (Falcon 3912-III, Bectin-Dickinson) was measured as previously described (23).

Immunostaining Glycolipids with Anti-LOS Monoclonal Antibody. Authentic paragloboside was detected on thin-layer chromatograms by immunostaining followed by autoradiography for 24 hours (24).

Results and Discussion

Figure 1A:
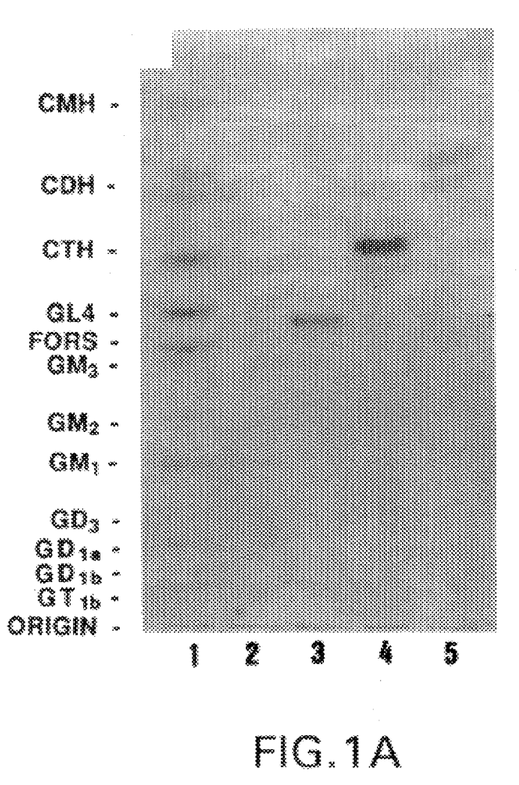
Figure 1B:
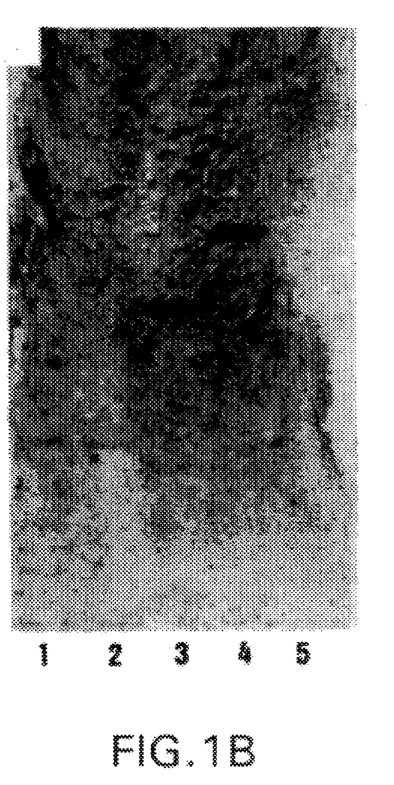
Figure 2:
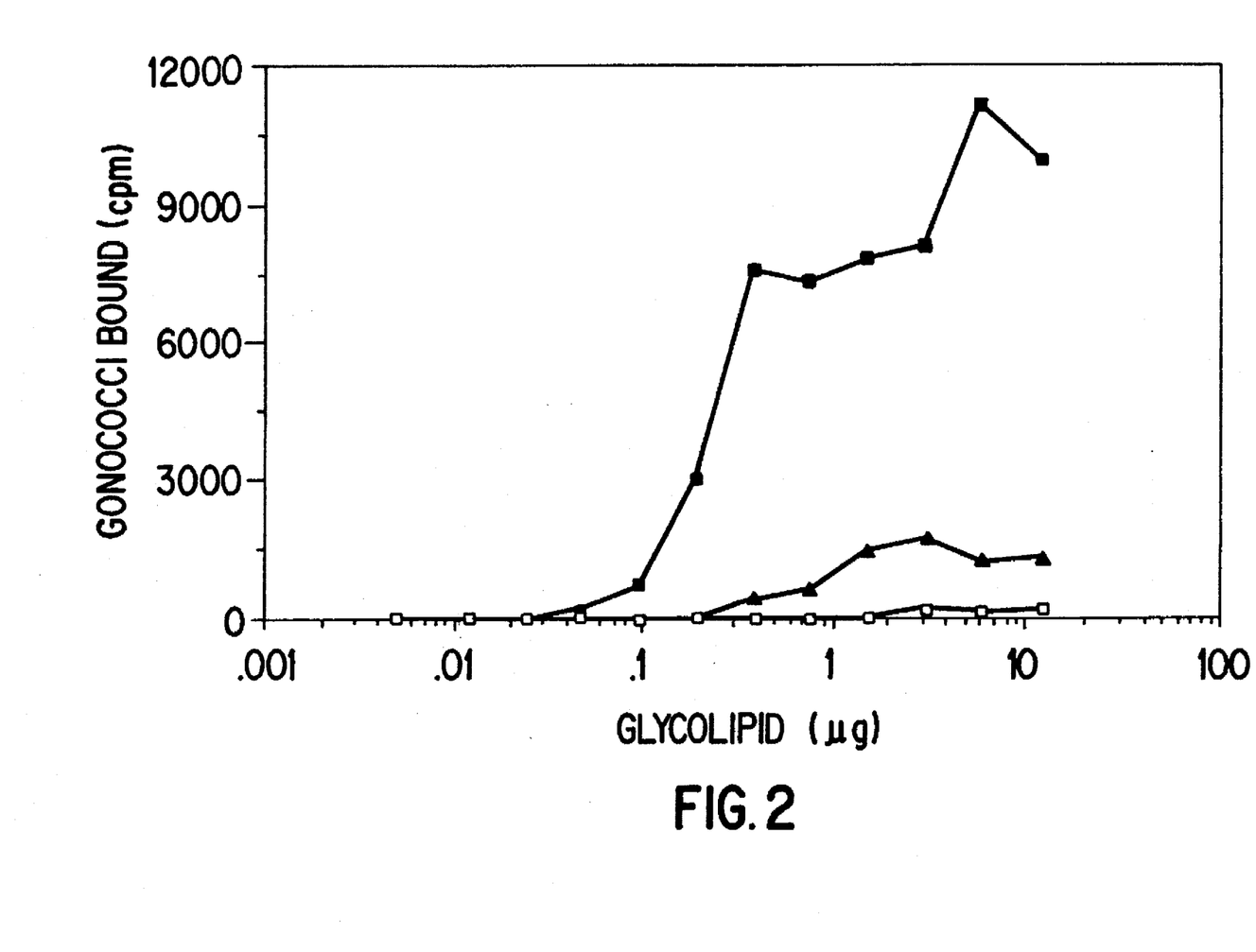

Binding of *N. gonorrhoeae* to Lacto-Series Glycolipids on Chromatograms. The glycolipid specificity of the different gonococcal isogenic variants was established by the thin-layer overlay assay and is summarized in Table II. As shown by an autoradiogram (FIG. 1B) compared with an identical thin-layer plate visualized with orcinol reagent (FIG. 1A), *N. gonorrhoeae* binds avidly to authentic paragloboside and the product obtained after B-galactosidase treatment, lacto-N-triaosylceramide (FIG. 1B, lanes 3 and 4). No binding wad detected to lactosylceramide derived from lacto-N-triaosylceramide after treatment with N-acetyl-B-hexosaminidase (FIG. 1B, lane 5), or to the other neutral glycolipids tested (FIG. 1B, lane 1; Table I). These data appear to be in variance with those of Stromberg et al. (12) who reported that *N. gonorrhoeae* does not bind to lacto-N-triaosylceramide and lacto-N-neotetraosylceramide (paragloboside). Possibly, this discrepancy is related to the source and/or fatty acid contents (12) of the glycolipids used by these investigators. In some experiments, *N. gonorrhoeae* bound weakly to some of the gangliosides (Table I), including sialylparagloboside (FIG. 1B, lane 2) and GM1 (FIG. 1B, lane 1); however, this observation was not always reproducible, and none of the gangliosides demonstrated concentration-dependent binding in microtiter plates (FIG. 2).

Quantitative Binding of *N. gonorrhoeae* to Immobilized Glycolipids and Inhibition of Binding by Glycolipids. Binding of *N. gonorrhoeae* to purified glycolipids adsorbed on microtiter plates was examined to further define the binding specificity and to compare the relative avidities of the lacto-and ganglio-series receptors. As shown in FIG. 2, the gonococci bind better to asialo-GM2 than to paragloboside and not at all to sialyparagloboside, GM2 is half-maximal at 0.2 ug, about 7 times better than to paraglobside (or lacto-N-triaosylceramide, data not shown), suggesting a higher avidity for the ganglio-series glycolipids. Binding of P+ and P− variants of *N. gonorrhoeae* to both asialo-GM1 and paragloboside was not affected by changing the growth conditions of the organism, as the gonococci bound equally well to both glycolipids when grown anaerobically, microaerophilically on agar or in broth, or under iron limited conditions (data not shown).

Biological Significance. *N. gonorrhoeae* agglutinate human erythrocytes (25) and adhere to and are phagocytozed by neutrophils (26). The receptor that mediates binding of these cells to the gonococci is probably paragloboside and lacto-N-triaosylceramide which are present in substantial amounts in both cell types (14,16,27). Lacto-series also constitute the major glycolipid component of various tissues and organs and are glycolipid precursors of the major blood group antigens. Interestingly, GalB1-4GlcNAcB1-4Glc . . . sequences are also present in may gonococcal LOS (15). As shown in FIG. 3, an anti-LOS antibody (4BE12) (18) binds strongly to authentic human paragloboside, detecting as little as 30 ng of glycolipid. Gonococcal lipopolysaccharide which contains the 4.8 kD LOS component is bound by monoclonal antibody 4BE12 thus confirming the presence of the GalB1-4GlcNAcB1-4GalB1-4Glc . . . sequence in this lipopolysaccharide (data not shown). This LOS also strongly inhibits gonococcal specific agglutination of human erythrocytes, as well as inhibits the binding of radiolabeled P+ and P− gonococci to paragloboside and lacto-N-triaosylceramide on thin-layer chromatograms (data not shown). Thus, the mechanism for the well-known phenomenon of gonococcal autoagglutination (29,30) may be explained by an adhesin of one organism binding to GlcNAcB1-3GalB1 . . . sequences in the LOS of another organism. As microorganismsl LOS do not contain ceramide, binding of N. gonorrhoea to at least the lacto-series glycolipids is probably not dependent on the fatty acid in ceramide as has been reported for other microorganisms (31).

Asialo-GM2 has been reported to occur in cultured human endocervical cells (12), a relevant target tissue for infection, and asialo-gangliosides also occur in other human tissues, although in lower amounts (14,32,33). Both asialo-GM1 and asialo-GM2, however, bind N. gonorrhoeae with highest avidity (FIG. 2). Recently, Paruchuri et al. (34) have identified the gene encoding for an adhesin which binds to asialo-GM1 and asialo-GM2 and have shown that the adhesin is 36 kD protein that is not associated with gonococcal pili. As mutants that do not express this adhesin retain their ability to agglutinate human erythrocytes (34), this adhesin probably is distinct from the paragloboside-binding specificity we describe here. Thus, more than one type of gonococcal adhesin may mediate binding to different human cell types and individually or coordinately contribute to the pathogensis of disease.

SUMMARY

The role glycolipids as adhesion receptors for *Neisseria gonorrhoeae* was examined. Serum resistant isolates, piliated and nonpiliated isogenic variants, as well as gonococci deficient in lipooligosacharide (LOS) and protein II, bound specifically to terminal and internal GlcNAcB1-3GalB1-4Glc sequences in lacto-series glycolipids, as measured by overlaying glycolipid chromatograms with $^{125}$I-labeled organisms. The binding activity was not affected by changing the growth condition of the organism, as the gonococci bound to the glycolipids when grown anaerobically, microaerophilically on agar or in broth, or under iron-limited conditions. The gonococci did not bind to lactosylceramide (GalB1-4GlcB1-1Cer) derived from lacto-N-triaosylceramide or from asialo-GM2 by treatment with N-acetyl-B-hexosaminidase, or to other neutral glycolipids tested. Although N. gonorrhoeae bound weakly to some gangliosides on thin-layer chromatograms, including sialylparagloboside and GM1, in solid phase assays the gonococci bound with moderate avidity to the sequence GlcNAcB1-3GalB1-4Glc and not at all to gangliosides. Interestingly, the 4.8 kD component of gonococcal LOS, which contains lacto-N-neotetraose (GalB1-4GlcNAcB1-3GalB1-4Glc), strongly inhibited gonococcal specific agglutination of human erythrocytes and inhibited the binding of labeled organisms to human paragloboside and lacto-N-triaosylceramide on thin-layer chromatograms. Possibly, this binding specificity explains why gonococci autoagglutinate in vitro.

EXAMPLE 2

Adhesion Receptors for Other Microorganisms

Figure 4A:
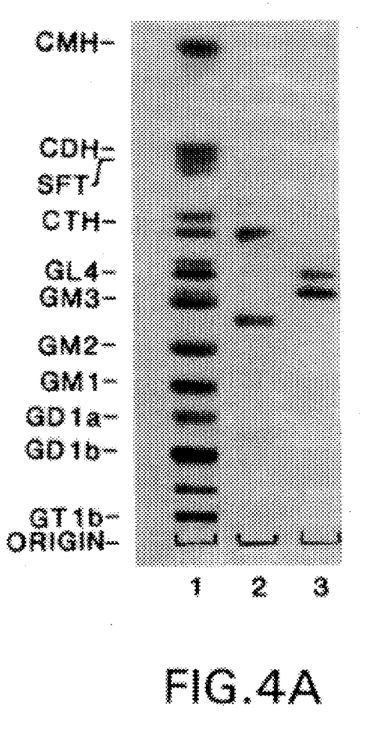
Figure 4B:
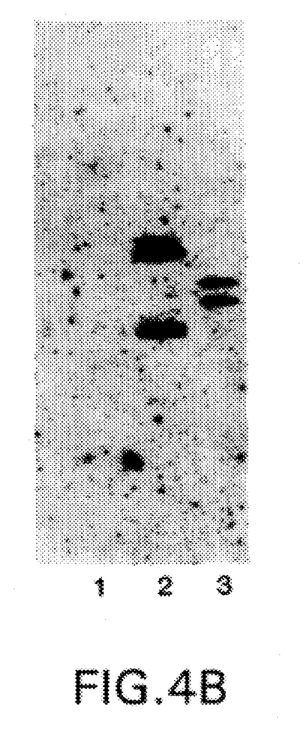

A wide variety of other microorganisms were tested according to the methods of Example 1 to determine their ability to bind to the receptors of the invention. Those organisms are identified in Table III. It was determined that such microorganisms bound to the receptor with the same range of affinity as the N. gonorrhoeae bound the receptors in Example 1. FIG. 4 is a representative example, showing the binding of *Pseudomonas aeruginosa* to paragloboside.

EXAMPLE 3

Purification of Bacterial Adhesin Protein

This example shows how to obtain the purified bacterial adhesin protein that binds to the receptors of the invention. The steps are as follows:

1. Growth of organism. A special defined medium, low methionine, is prepared, and 75 ml of this fresh media in a 100 ml glass sterile bottle is innoculated with the organism. Then 0.5 mCi of $^{35}$S-methionine is added. The organism is grown at 37° C., 5% $CO_2$ for 24 hrs.

2. Harvest of organism. After 24 hrs. the organism is centrifuged 10,000×g for 10 min. at 4° C. The pellet is resuspended in 20 ml of 10 mM Hepes pH 7.4, saline and put on ice.

3. Preparation of Omps. The resuspended organism is sonicated 6 times on ice for 30 seconds each at a setting of 4 on the Bronson Sonicator. Then the disrupted organism is centrifuged 10,000×g for 10 min. at 4° C. The supernatant is centrifuged 100,000×g for 30 min. at 4° C. The resulting pellet is called Omps. Protease inhibitors are added (PIC 1+11) and stored for 2 weeks at 4° C.

4. Solubilization of Omps. Omps are centrifuged 100,000×g as above. The pellet is resuspended in 4 ml of 10 mM Hepes pH 8.0, 1.3% Octyl-Glucopyranoside (Sigma), sonicated for 5 minutes, and incubated at room temperature for 30 minutes. Then the Omps are centrifuged at 100,000×g as before. The resulting supernatant contains soluble adhesin.

5. Purification of Adhesin Protein. The adhesin is purified from the octylglucopuroanoside supernatant by diluting it 1/10 in 50 mM Tris-HCl pH 7.8, 150 mM NaCl, 1.0% BSA and incubating it in previously blocked wells of an ELISA plate containing 0.8 ug/well of receptor for 2 hrs. at room temperature. Wells are washed 4× with cold normal saline, then 30 ul of 60° C. 10 mM Tris-HCl, pH 8.0, saline, 0.1% SDS is added to each well and incubated for 30 min. at 37° C. Alternatively, the adhesin is purified by receptor affinity column chromatography, where the receptor is immobilized as an insoluble support like agarose beads. The SDS elution buffer is removed from appropriate wells and analyzed on SDS-PAGE and autoradiography.

TABLE I

Glycolipids Tested for Ability to Bind *N. gonorrhoeae* on Thin-Layer Chromatograms

| Glycolipid[a] | Structure | Binding[b] |
|---|---|---|
| Asialo-GM2 | GalNAcB1-4GalB1-4GlcB1-1Cer | ++ |
| Asialo-GM1 | GalB1-3GalNAcB1-4GalB1-4GlcB1-1Cer | ++ |
| Lactotriaosylcer | GlcNAcB1-3GalB1-4GlcB1-1Cer | + |
| Paragloboside | GalB1-4GlcNAcB1-3GalB1-4GlcB1-1Cer | + |
| Glucosylcer (CMH) | GlcB1-1Cer | − |
| Lactosylcer (CDH) | GalB1-4B1c-1Cer | − |
| Trihexosylcer (CTH) | Gala1-4GalB1-GlcB-1Cer | − |
| Globoside (GL4) | GalNAcB1-3Gala1-4GalB1-4GlcB1-1Cer | − |
| Forssman (Fors) | GalNAca1-3GalNAcB1-3Gala1-4GalB1-4GlcB-1-Cer | − |
| GM3 | NeuAca2-3GalB1-4GlcB1-1Cer | − |
| GM2 | GalNAcB1-4 [NeuAca2-3]GalB1-4GlcB1-1Cer | − |
| GM1 | GalB1-3GalNAcB1-4 [NeuAca2-3]GalB1-4GlcB1-1Cer | +/− |
| Sialylparagloboside | NeuAcaGalB1-4GlcNAcB1-3GalB1-4GlcB1-1Cer | +/− |
| GD3 | NeuAca2-8NeuAca2-3GalB1-4GlcB1-1Cer | +/− |
| GD1a | NeuAca2-3GalB1-3GalNAcB1-4 [NeuAca2-3GalB1-4GlcB1-1Cer | +/− |
| GD1b | GalB1-3GalNAcB1-4 [NeuAca2-8NeuAca2-3]GalB1-4GlcB1-1Cer | +/− |
| GT1b | NeuAca2-3GalB1-3GalNAcB1-4 [NeuAca2-8NeuAca2-3GalB1-4GlcB1-1Cer | − |

[a]Trivial names and structures are represented according to recommendations in Ref 38 and references cited therein; cer, ceramide; CMH, ceramide monohexoside; CDH, ceramide dihexoside (lactosylceramide); CTH, ceramide trihexoside; GL4, globoside.
[b]Negative binding (−) indicates no binding to 2 ug of glycolipid and positive binding to less than 0.4 ug (++), 0.8–1 ug(+), and 1 ug(+/−).

TABLE II

*N. gonorrhoeae* Strains Used in This Study and Their Glycolipid Binding Specificities[a]

| | | Binding to | |
|---|---|---|---|
| Strain (Ref.) | Phenotype[b] | Asialo-GM1 | Paragloboside |
| MS11$_{mk}$ (34) | P+, PII− | ++ | + |
| MS11$_{mk}$ (34) | P−, PII− | ++ | + |
| FA5100 (35) | LOS−/MAb unreactive | ++ | + |
| WG-52 (36) | serum resistant | ++ | + |

[a]Determined by the microorganisms1 overlay assay using 0.5 ug of purified asialo-GM1 or 1 ug paragloboside as described in Materials and Methods.
[b]Abbreviations used: P+, piliated; P−, nonpiliated; PII; protein II deficient; LOS−, Lipooligosaccahride deficient; MAb, monoclonal antibody.

TABLE III

Other Pathogenic and Opportunistic Microorganisms That Bind to the Receptors Lactotriaosylcer and Paragloboside

| | |
|---|---|
| *Streptococcus pneumoniae* | *Neisseria gonorrhoeae* |
| *Streptococcus agalactiae* (Gp.B) | *Neisseria meningitidis* |
| *Staphylococcus aureus* | *Shigella dysenteriae* |
| *Clostridium perfringens* | *Shigella flexneri* |
| *Borrelia burgdorferi* (Lyme agent) | *Coxiella burnettii* |
| *Clostridium difficile* | *Pseudomonas aeruginosa* |
| *Haemophilus influenzae* | *Pseudomonas cepacia* |
| *Haemophilus parainfluenzae* | *Pseudomonas maltophilia* |

REFERENCES

1. Savage, D. C. (1977) Annu. Rev. Microbiol. 31:107–133.
2. Beachey, E. H. (ed) (1980) Bacterial Adherence. Receptors and Recognition, Series B, Vol. 8. Chapman and Hall, New York.
3. Jones, G. W., and Isaacson, E. (1983) CRC Crit. Rev. Microbiol. 34:228–260.
4. Calander, N., Karlsson, K. A., Nyholm, P.-G. and Pascher, I. (1988) Biochimie 70:1673–1682.
5. Bock, K., Breimer, M. E., Brignole, A., Hansson, G. C., Karlsson, K. A., Larson, G., Leffler, H., Samuelsson, B. E., Stromberg, N., Svanborg-Eden, C., and Thurin, J., (1985) J. Biol. Chem. 260:8545–8551.
6. Stromberg, N., Ryd, M., Lindberg, A. A., and Karlson, K. A. (1988) FEBS Lett. 232:193–198.
7. Stromberg, N., and Karlsson, K. A. (1990) J. Biol. Chem. 265:11244–11250.
8. Karivan, H. C., Roberts, D. D., and Ginsburg, V. (1988) Proc. Natl. Acad. Sci 85:6157–6116.
9. Krivan, H. C., Olson, L. D., Barile, M. F., Ginsburg, V. and Roberts, D. D. (1989) J. Biol. Chem. 264:9283–9288.
10. Andersson, et al. (1983) J. Exp. Med. 559–570.
11. Andersson, et al. (1988) Monogr. Allergy 24:44–45.
12. Stromberg, N., Deal, C. Nyberg, G., Normark, S., So. M., and Karlsson, K. A. (198B) Proc. Natl. Acad. Sci. 85:4902–4906.
13. Paruchuri, D. K., Seifert, H. S., Ajioka, R. S., Karlsson, K. A., and So, M. (1990) Proc. Natl. Acad. Sci. 87:333–337.
14. Krivan, H. C., Roberts, D. D. , and V. Ginsburg. (1988) Proc. Natl. Acad. Sci. 85, 6157–6161.
15. Mandrell, R. E., Griffiss, J. M., and Macher, B. A. (1988) J. Exp. Med. 168, 107–126.
16. Bertram, M. A., Griffis, J. M., and Broud, D. D. (1976) J. Immunol. 116, 842–846.
17. Westphal, O., and Jann, K. (1965) in Methods in Carbohydrate Chemistry (Whistler, R. L., ed.), pp. 83–91.
18. Zollinger, W. D. and Mandrell, R. E. (1980) Infect. Immun. 28, 451–458.
19. Fraker, P. J., and Speck J. C. (1978) Biochem. Biophys. Res. Commun. 80, 849–857.
20. Ando, S., Kon, K., Isobe, M., Nagai, Y., and Yamakawa, T. (1976) J. Biochem. (Tokyo) 79, 625–532.
21. Knapp, J. S., and Clark, V. L. (1984) Infect. Immun. 46, 1766–181.
22. Mickelson, P. A., Blackman, E., and Sparling, P. F. (1982) Infect. Immun. 35, 915–920.
23. Krivan, H. C., Ginsburg, V., and Roberts, D. D. (1988) Arch. Biochem. Biophys. 260, 493–496.
24. Magnani, J. L., Spitalnik, S. L., Ginsburg, V. (1987) Meth. Enzymol. 138, 195–207.
25. Wiseman, G. M., McNicol, P., Lian, C. J., and Primrose, D. S. (1981) Can. J. Microbiol. 27, 1035–1043.

26. Shafer, W. M., and Rest, R. F. (1989) Ann. Rev. Microbiol. 121–145.
27. Macher, B. A., and Klock, J. C. (1980) J. Biol. Chem. 255, 2092–2096.
28. Siddiqui, B., and Hakormori, S. (1973) BioChem. Biophys. Acta 330, 147–155.
29. Swanson, J. L., S. J. Kraus, and E. C. Gotschlich 1971. J. Exp. Med. 134, 886–906.
30. Swanson, J. L. (1978) Infect. Immun. 19, 320–331.
31. Stromberg, N., Ryd, M., Lindberg, A., and Karlsson, K. A. (1988) FEBS Lett. 232, 193–198.
32. Spitalnik, P. F., Danley, J. M., Burger, S. R., and Spitalnik, S. L. (1989) Arch. Biochem. Biophys. 273, 578–591.
33. Gillard, B. K., Jones, M. A., and Marcus, D. M. (1987) Arch. BioChem. Biophys. 256, 435–445.
34. Paruchuri, D. K., Seifert, H. S., Ajioka, R. S., Karlsson, K. -A., and So., M. (1990) Proc. Natl. Acad. Sci. U.S.A. 87, 333–337.
35. Swanson, J. Barrera, O., Sola, J., Boslego, J. (1988) J. Exp. Med. 168, 2121–2129.
36. Shafer, W. M., Joiner, K., Guymon, L. F., Cohen, M. S., and Sparling P. F. (1984) J. Infect. Dis. 149, 175–183.
37. Rice, P. A., Kasper, D. L. (1987) J. Clin. Invest. 60, 1149–1158.
38. IUPAC-IUB Joint Commission on Biochem. Nomencl. (1986) Eur. J. Biochem. 159, 1–6.

We claim:

1. A method for detecting the presence of pathogenic or opportunistic microorganisms selected from the group consisting of *Streptococcus agalactiae, Clostridium, Borrelia, Haemophilus parainfluenzae, Pseudomonas cepacia, Pseudomonas maltophilia, Neisseria meningitidis*, Coxiella, and Shigella in a sample suspected of containing said microorganisms comprising the steps of:

contacting said sample with one or more receptors comprising a substantially pure compound selected from the group consisting of Galβ1-4GlcNAcβ1-3Galβ1-4Glcβ1-1-X(R), Galβ1-3GlcNAcβ1-3Galβ1-4Glcβ1-1-X(R), GlcNAcβ1-3Galβ1-4Glcβ1-1-X(R), Galβ1-4GlcNAcβ1-3Galβ1-4Glc, Galβ1-3GlcNAcβ1-3Galβ1-4Glc, GlcNAcβ1-3Galβ1-4Glc, Galβ1-4GlcNAcβ1-3Gal, Galβ1-3GlcNAcβ1-3Gal wherein X is sphingosine, hydroxylated sphingosine or saturated sphingosine and R is H or an N-acetyl fatty acid derivative of X such that X(R) is a ceramide for a period of time and under conditions sufficient for said receptors to bind to said microorganisms if said microorganisms are present in said sample; and determining if said receptors has/have bound to said microorganisms.

2. The method of claim 1 wherein said receptor is attached to an insoluble substrate.

3. The method of claim 2 wherein said step of determining if said receptor has bound to said microorganisms comprises the steps of:

contacting any receptor-microorganism complexes formed by the method of claim 2 with an antibody which binds to an antigen on the surface of said microorganisms, wherein said antibody is labeled with a detectable moiety, thereby forming receptor-microorganism-antibody complexes;

removing unbound antibody; and detecting the presence of said detectable moiety.

4. A diagnostic kit for the detection of pathogenic or opportunistic microorganisms selected from the group consisting of *Streptococcus agalactiae, Clostridium, Borrelia, Haemophilus parainfluenzae, Pseudomonas cepacia, Pseudomonas maltophilia, Neisseria meningitidis*, Coxiella and Shigella in a sample suspected of containing said microorganisms comprising, in a container:

one or more receptors comprising a substantially pure compound selected from the group consisting of Galβ1-4GlcNAcβ1-3Galβ1-4Glcβ1-1-X(R), Galβ1-3GlcNAcβ1-3Galβ1-4Glcβ1-1-X(R), GlcNAcβ1-3Galβ1-4Glcβ1-1-X(R), Galβ1-4GlcNAcβ1-3Galβ1-4Glc, Galβ1-3GlcNAcβ1-3Galβ1-4Glc, GlcNAcβ1-3Galβ1-4Glc, Galβ1-4GlcNAcβ1-3Gal, and Galβ1-3GlcNAcβ1-3Gal wherein X is sphingosine, hydroxylated sphingosine or saturated sphingosine and R is H or an N-acetyl fatty acid derivative of X such that X(R) is a ceramide attached to an insoluble substrate; and a reagent comprising a detectable moiety and which binds to said microorganisms for detecting or measuring the formation of complexes of said microorganisms and said receptor(s).

5. The kit of claim 4 wherein said reagent comprising a detectable moiety is one or more receptors comprising a substantially pure compound selected from the group consisting of Galβ1-4GlcNAcβ1-3Galβ1-4Glcβ1-1-X(R), Galβ1-3GlcNAcβ1-3Galβ1-4Glcβ1-1-X(R), GlcNAcβ1-3Galβ1-4Glcβ1-1-X(R), Galβ1-4GlcNAcβ1-3Galβ1-4Glc, Galβ1-3GlcNAcβ1-3Galβ1-4Glc, GlcNAcβ1-3Galβ1-4Glc, Galβ1-4GlcNAcβ1-3Gal, Galβ1-3GlcNAcβ1-3Gal wherein X is sphingosine, hydroxylated sphingosine or saturated sphingosine and R is H or an N-acetyl fatty acid derivative of X such that X(R) conjugated with a detectable moiety.

6. The kit of claim 4 wherein said reagent is an antibody which binds to a surface antigen of said microorganisms conjugated to an enzyme.

7. The kit of claim 4 wherein said reagent comprises a first antibody which binds to a surface antigen of said bacterium and a second antibody which binds to said first antibody, wherein said second antibody is conjugated to said detectable moiety.

8. The kit of claim 4, wherein said detectable moiety is selected from the group consisting of an enzyme, radioisotope, fluorescent and chemiluminescent entity.

9. A method for detecting the microorganism *Neisseria gonorrhoeae* in a sample suspected of containing said microorganism comprising the steps of:

contacting said sample with a receptor comprising a substantially pure Galβ1-4GlcNAcβ1-3Galβ1-4Glcβ1-1-Cer which has been isolated from erythrocytes, for a period of time and under conditions sufficient for said receptor to bind to said microorganism if said microorganism is present in said sample; and determining if said receptor has bound to said microorganism.

10. The method in claim 9 wherein said receptor is attached to an insoluble substrate.

11. The method of claim 10 wherein said step of determining if said receptor has bound to said microorganism comprises the steps of:

contacting any receptor-microorganism complexes formed by the method of claim 10 with an antibody which binds to an antigen on the surface of said microorganism, wherein said antibody is labeled with a detectable moiety, thereby forming receptor-microorganism-antibody complexes;

removing unbound antibody; and detecting the presence of said detectable moiety.

12. A diagnostic kit for the detection of the microorganism *Neisseria gonorrhoeae* in a sample suspected of containing said microorganism comprising, in a container:

a receptor comprising a substantially pure Galβ1-4GlcNAcβ1-3Galβ1-4Glcβ1-1-Cer which has been isolated from erythrocytes; and a reagent comprising a detectable moiety and which binds to said microorganism for detecting or measuring the formulation of complexes of said microorganism and said receptor.

13. The kit of claim 12 wherein said reagent comprising a detectable moiety is a receptor comprising a substantially pure Galβ1-4GlcNAcβ1-3Galβ1-4Glcβ1-1-Cer which has been isolated from erythrocytes.

14. The kit of claim 12 wherein said reagent is an antibody which binds to a surface antigen of said microorganism conjugated to an enzyme.

15. The kit of claim 12 wherein said reagent comprises a first antibody which binds to a surface antigen of said bacterium and a second antibody which binds to said first antibody, wherein said second antibody is conjugated to said detectable moiety.

16. The kit of claim 12, wherein said detectable moiety is selected from the group consisting of an enzyme, radioisotope, fluorescent and chemiluminescent entity.

17. A method for detecting the presence of pathogenic or opportunistic microorganisms selected from the group consisting of Staphylococcus spp., Haemophilus spp. and Pseudomonas spp. in a sample suspected of containing said microorganisms comprising the steps of:

contacting said sample with one or more receptors comprising a substantially pure compound selected from the group consisting of Galβ1-3GlcNAcβ1-3Galβ1-4Glcβ1-1-X(R), GlcNAcβ1-3Galβ1-4Glcβ1-1-X(R), Galβ1-4GlcNAcβ1-3Galβ1-4Glc, Galβ1-3-GlcNAcβ1-3Galβ1-4Glc, GlcNAcβ1-3Galβ1-4Glc, Galβ1-4GlcNAcβ1-3Gal, Galβ1-3GlcNAcβ1-3Gal wherein X is sphingosine, hydroxylated sphingosine or saturated sphingosine and R is H or an N-acetyl fatty acid derivative of X such that X(R) is a ceramide for a period of time and under conditions sufficient for said receptor(s) to bind to said microorganisms if said microorganisms are present in said sample; and determining if said receptor(s) has/have bound to said microorganisms.

18. The method in claim 17 wherein said receptor is attached to an insoluble substrate.

19. The method of claim 18 wherein said step of determining if said receptor has bound to said microorganisms comprises the steps of:

contacting any receptor-microorganism complexes formed by the method of claim 18 with an antibody to an antigen which binds on the surface of said microorganisms, wherein said antibody is labeled with a detectable moiety, thereby forming receptor-microorganism-antibody complexes;

removing unbound antibody; and detecting the presence of said detectable moiety.

20. A diagnostic kit for the detection of pathogenic or opportunistics microorganisms selected from the group consisting of Staphylococcus spp., Haemophilus spp. and Pseudomonas ssp. in a sample suspected of containing said microorganisims comprising, in a container:

one or more receptor comprising, a substantially pure compound selected from the consisting of Galβ1-3GlcNAcβ1-3Galβ1-4Glcβ1-1-X(R), GlcNAcβ1-3Galβ1-4Glcβ1-1-X(R), Galβ1-4GlcNAcβ1-3Galβ1-4Glc, Galβ1-3-GlcNAcβ1-3Galβ1-4Glc, GlcNAcβ1-3Galβ1-4Glc, Galβ1-4GlcNAcβ1-3Gal, and Galβ1-3-GlcNAcβ1-3Gal wherein X is sphingosine, hydroxlated sphingosine or saturated sphingosine and R is H or an N-actyl fatty acid derivate of X such that X(R) is ceramide attached to an insoluble substrated; and a reagent comprising a detectable moiety and which binds to said microorganisms for detecting or measuring the formation of complexes of said microorganisms and said receptor(s).

21. The kit of claim 20 wherein said reagent comprising a detectable moiety is one or more receptors comprising a substantially pure compound selected from the group consisting of Galβ1-3GlcNAcβ1-3Galβ1-4Glcβ1-1-X(R), GlcNAcβ1-3Galβ1-4Glcβ1-1-X(R), Galβ1-4GlcNAcβ1-3Galβ1-4Glc, Galβ1-3GlcNAcβ1-3Galβ1-4Glc, GlcNAcβ1-3Galβ1-4Glc, Galβ1-4GlcNAcβ1-3Gal, Galβ1-3GlcNAcβ1-3Gal wherein X is sphingosine, hydroxylated sphingosine or saturated sphingosine and R is H or an N-acetyl fatty acid derivative of X such that X(R) conjugated with a detectable moiety.

22. The kit of claim 20 wherein said reagent is an antibody which binds to a surface antigen of said microorganism conjugated to an enzyme.

23. The kit of claim 20 wherein said reagent comprises a first antibody which binds to a surface antigen of said bacterium and a second antibody which binds to said first antibody, wherein said second antibody is conjugated to said detectable moiety.

24. The kit of claim 20, wherein said detectable moiety is selected from the group consisting of an enzyme, radioisotope, fluorescent and chemiluminescent entity.

25. The kit of claim 4 wherein said insoluble substrate is the well of a microtiter plate.

26. The kit of claim 20 wherein said insoluble substrate is the well of a microtiter plate.

* * * * *